US009928607B2

(12) United States Patent
Jeanne et al.

(10) Patent No.: US 9,928,607 B2
(45) Date of Patent: Mar. 27, 2018

(54) DEVICE AND METHOD FOR OBTAINING A VITAL SIGNAL OF A SUBJECT

(71) Applicant: KONINKLIJKE PHILIPS N.V., Eindhoven (NL)

(72) Inventors: Vincent Jeanne, Bothell, WA (US); Marinus Bastiaan Van Leeuwen, Eindhoven (NL); Michel Jozef Agnes Asselman, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 50 days.

(21) Appl. No.: 15/028,791

(22) PCT Filed: Oct. 15, 2014

(86) PCT No.: PCT/EP2014/072102
§ 371 (c)(1),
(2) Date: Apr. 12, 2016

(87) PCT Pub. No.: WO2015/055709
PCT Pub. Date: Apr. 23, 2015

(65) Prior Publication Data
US 2016/0253820 A1    Sep. 1, 2016

(30) Foreign Application Priority Data
Oct. 17, 2013    (EP) .................................... 13189044

(51) Int. Cl.
*G06K 9/00*    (2006.01)
*G06T 7/20*    (2017.01)
(Continued)

(52) U.S. Cl.
CPC ............ *G06T 7/204* (2013.01); *A61B 5/0059* (2013.01); *A61B 5/0077* (2013.01);
(Continued)

(58) Field of Classification Search
CPC ... A61B 5/0059; A61B 5/0077; A61B 5/0082; A61B 5/02416; A61B 5/1114;
(Continued)

(56) References Cited

U.S. PATENT DOCUMENTS

| 5,704,367 A | 1/1998 | Ishikawa |
| 2010/0061596 A1 | 3/2010 | Mostafavi |

(Continued)

FOREIGN PATENT DOCUMENTS

| CN | 102309318 | 1/2012 |
| EP | 2438849 | 4/2012 |
| WO | 2011/042858 | 4/2011 |

OTHER PUBLICATIONS

Verkruysse, et al., "Remote plethysmographic imaging using ambient light", Optics Express, vol. 16, No. 26, Dec. 2008.
(Continued)

*Primary Examiner* — Li Liu

(57) ABSTRACT

The present invention relates to a device for obtaining a vital sign of a subject, comprising an interface (20) for receiving a set of image frames of a subject, a motion analysis unit (30) for analyzing at least one measurement area within the image frames of the set of image frames and for characterizing motion of the subject within the set of image frames, a signal extraction unit (40) for extracting photoplethysmographic, PPG, signals from the set of image frames using the characterization of motion of the subject within the set of image frames, and a vital signs determination unit (50) for determining vital sign information from the extracted PPG signals. The motion analysis unit comprises a motion estimation unit (32), a spatial characteristic extraction unit (34), and a motion characterization unit (36).

20 Claims, 3 Drawing Sheets

(51) Int. Cl.
*A61B 5/00* (2006.01)
*A61B 5/024* (2006.01)
*A61B 5/11* (2006.01)
*G06T 7/00* (2017.01)
*G06T 7/223* (2017.01)
*G06T 7/246* (2017.01)
*G06T 7/90* (2017.01)

(52) U.S. Cl.
CPC ........ *A61B 5/0082* (2013.01); *A61B 5/02416* (2013.01); *A61B 5/1114* (2013.01); *A61B 5/1128* (2013.01); *A61B 5/7207* (2013.01); *A61B 5/7221* (2013.01); *G06T 7/0012* (2013.01); *G06T 7/20* (2013.01); *G06T 7/223* (2017.01); *G06T 7/248* (2017.01); *G06T 7/90* (2017.01); *G06T 2207/10016* (2013.01); *G06T 2207/10024* (2013.01); *G06T 2207/20021* (2013.01); *G06T 2207/20056* (2013.01); *G06T 2207/30004* (2013.01); *G06T 2207/30076* (2013.01); *G06T 2207/30088* (2013.01); *G06T 2207/30196* (2013.01); *G06T 2207/30201* (2013.01); *G06T 2207/30232* (2013.01)

(58) Field of Classification Search
CPC ... A61B 5/1128; A61B 5/7207; A61B 5/7221; G06T 2207/10016; G06T 2207/10024; G06T 2207/20021; G06T 2207/30004; G06T 2207/30076; G06T 2207/30088
See application file for complete search history.

(56) References Cited

U.S. PATENT DOCUMENTS

| | | | |
|---|---|---|---|
| 2011/0251493 A1 | 10/2011 | Poh | |
| 2012/0195437 A1* | 8/2012 | Van den Heuvel | H04R 25/30 381/60 |
| 2012/0195469 A1* | 8/2012 | Kirenko | G06T 7/20 382/103 |
| 2012/0197137 A1* | 8/2012 | Jeanne | A61B 5/02028 600/479 |
| 2012/0289850 A1 | 11/2012 | Xu | |
| 2014/0205175 A1* | 7/2014 | Tanaka | G01J 3/0264 382/134 |
| 2014/0275832 A1* | 9/2014 | Muehlsteff | A61B 5/0205 600/301 |

OTHER PUBLICATIONS

Poh, et al., "Advancements in Noncontact, Multiparameter Physiological Measurements Using a Webcam", IEEE Transactions on Biomedical Engineering, vol. 58, No. 1, January 2011.

Al-Khalidi, et al., "Facial Tracking Method for Noncontact Respiration Rate Monitoring", 2010 IEEE.

Sun, et al., "Motion-compensated noncontact imaging photoplethysmography to monitor cardiorespiratory status during exercise", J. Biomed. Opt. 16(7), 077010 (Jul. 18, 2011).

Yaying, et al., "Respiratory Rate Estimation via Simultaneously Tracking and Segmentation", 2010 IEEE.

Sahindrakar, "Improving Motion Robustness of Contact-less Monitoring of Heart Rate Using Video Analysis", Aug. 24, 2011.

* cited by examiner

  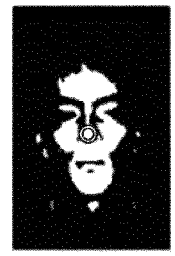 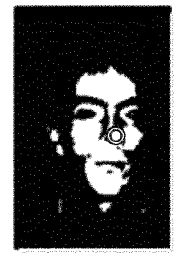
FIG. 2A  FIG. 2B  FIG. 2D  FIG. 2E
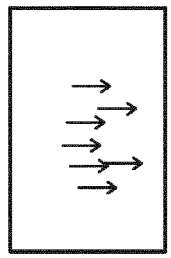 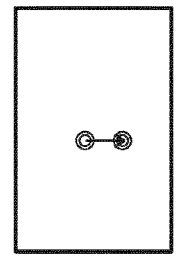
FIG. 2C  FIG. 2F
   
FIG. 3A  FIG. 3B  FIG. 3D  FIG. 3E
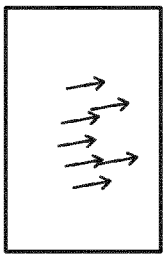 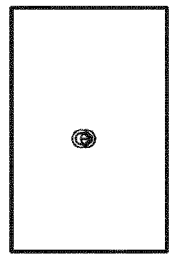
FIG. 3C  FIG. 3F

DEVICE AND METHOD FOR OBTAINING A VITAL SIGNAL OF A SUBJECT

CROSS REFERENCE TO RELATED APPLICATIONS

This application is the U.S. National Phase application under 35 U.S.C. § 371 of International Application No. PCT/EP2014/072102, filed Oct. 14, 2014, published as WO 2015/055709 on Apr. 23, 2015, which claims the benefit of European Patent Application Number 13189044.4 filed Oct. 17, 2013. These applications are hereby incorporated by reference herein.

FIELD OF THE INVENTION

The present invention relates to a device and a method for obtaining a vital sign of a subject. In particular, the present invention relates to an unobtrusive optical measurement approach which can be used for detecting vital signs in an observed subject, such as a person or animal.

BACKGROUND OF THE INVENTION

WO 2011/042858 discloses a method of processing a signal including at least a component representative of a periodic phenomenon in a living being includes obtaining at least one first signal having at least a component representative of a periodic phenomenon in a living being. Separate data representative of at least a periodic component of motion of the living being are obtained by obtaining a sequence of images showing the living being, synchronized with the at least one first signal, and carrying out video-based motion analysis of the sequence of images. The data are used at least to suppress a component of the first signal corresponding to the periodic component of motion of the living being.

US 2010/0061596 discloses a method of determining a similarity with a portion of a physiological motion, includes obtaining a first image of an object, obtaining a second image of the object, determining a level of similarity between the first and second images, and correlating the determined level of similarity between the first and second images with a portion of the physiological motion. A computer product having a set of instructions, an execution of which causes a method of determining a similarity with a portion of a physiological motion to be performed, the method includes obtaining a first image of an object, obtaining a second image of the object, determining a level of similarity between the first and second images, and correlating the determined level of similarity between the first and second images with a portion of the physiological motion.

Vital signs of a person, for example the heart rate (HR), blood oxygen saturation (SpO2) or respiratory information (respiratory parameters) such as the respiratory rate (RR), can serve as a powerful predictor of serious medical events. For this reason the respiratory rate and/or the heart rate are often monitored online in intensive care units or in daily spot checks in the general ward of a hospital. Besides the heart rate, the respiratory rate is one of the most important vital signs. Both, the HR and the RR are still difficult to measure without having direct body contact. In present intensive care units, thorax impedance plethysmography or the respiratory inductive plethysmography are still the methods of choice for measuring the RR, wherein typically two breathing bands are used in order to distinguish thorax and abdominal breathing motion of a person. The HR is typically measured by use of electrodes, fixed at the chest of the subject, wherein the electrodes are connected to remote devices through cables. However, these obtrusive methods are uncomfortable and unpleasant for the patient being observed.

It has been shown that one or more video cameras can be used for unobtrusively monitoring the HR, the RR or other vital signs of a subject by use of remote photoplethysmographic (remote PPG) imaging. Remote photoplethysmographic imaging is, for instance, described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while the pixel average over a selected region (typically part of the cheek in this system) is calculated. By looking at periodic variations of this average signal, the heart rate and respiratory rate can be extracted. There are meanwhile a number of further publications and patent applications that describe details of devices and methods for obtaining vital signs of a patient by use of remote PPG.

Thus, the pulsation of arterial blood causes changes in light absorption. Those changes observed with a photodetector (or an array of photodetectors) form a PPG (photoplethysmography) signal (also called, among other, a pleth wave). Pulsation of the blood is caused by the beating heart, i.e. peaks in the PPG signal correspond to the individual beats of the heart. Therefore, a PPG signal inherently includes a heart rate signal. The normalized amplitude of this signal is different for different wavelengths, and for some wavelengths it is also a function of blood oxygenation or other substances found in blood or tissue.

Compared to conventional contact sensors used for measuring heart rate, respiration and SpO2, which are attached to the subject and who's main source of noise is motion, the main advantages of camera-based vital signs monitoring is the high ease-of-use since there is no need to attach a sensor but the camera just needs to be aimed at the appropriate region of interest, e.g. a skin or chest region of the subject. Another advantage of camera-based vital signs monitoring is the potential for achieving motion robustness since cameras have a significant spatial resolution while contact sensors mostly comprise a single element detector.

One of the key challenges for the remote PPG technology is to be able to provide robust measurement during subject motion, in particular to provide a full motion robust solution.

SUMMARY OF THE INVENTION

It is an object of the present invention to provide a device and a method and system for obtaining a vital sign of a subject despite motion of the subject. The invention is defined by the independent claims.

In a first aspect of the present invention a device for obtaining a vital sign of a subject is presented that comprises
 an interface for receiving a set of image frames of a subject;
 a motion analysis unit for analysing at least one measurement area within the image frames of said set of image frames and for characterizing motion of the subject within said set of image frames, said motion analysis unit comprising a motion estimation unit for locally and/or globally estimating motion of the subject based on spatial similarities of pixels or pixel groups over consecutive image frames, a spatial characteristic extraction unit for globally extracting motion of the subject based on a displacement of a spatial characteristic of a group of pixels exhibiting the same or similar properties, and a motion characterization unit for determining the type of motion of the subject within said set of image frames based on the outputs of said motion estimation unit and said spatial characteristic extraction unit;

a signal extraction unit for extracting photoplethysmographic, PPG, signals from said set of image frames using said characterization of motion of the subject within said set of image frames; and a vital signs determination unit for determining vital sign information from said extracted PPG signals In a second aspect of the present invention a corresponding method for obtaining a vital sign of a subject is presented.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

The tracking algorithms for tracking an ROI for obtaining PPG signals from it that have been proposed so far provide good tracking ability when the motion of the tracked subject is in the camera plane, e.g. if there is a face translation (the face corresponding to the ROI or including the ROI). When the motion is out of the camera plane, e.g. if there is a face rotation, some existing image data simply disappear while other image data appear making the tracking very difficult or even impossible. This severely impacts the extraction of accurate PPG signals. Hence, the present invention is based on the idea to characterize the motion of the subject being monitored (in an embodiment to characterize in plane vs. out of plane motion) and to process obtained image data in a way ensuring optimal performance using automatic outliers rejection based on the observed motion. Further, by being able to detect when a correct measurement can be operated the proposed device and method also provide a reliability indication indicating the reliability of obtained PPG signals and/or derived vital signs.

According to a preferred embodiment said signal extraction unit is configured to extract said PPG signals only from image frames showing no or substantially no out-of-plane motion or for replacing parts of said PPG signals extracted from image frames showing out-of-plane motion by interpolated signal parts. This ensures that the derived vital signs are highly reliable and accurate.

In another embodiment said signal extraction unit is configured to reduce the size of the at least one measurement area (also referred to as ROI herein), from which PPG signals are extracted, in case of out-of-plane motion of the subject, in particular to extract PPG signals only from a central area of the at least one measurement area. This ensures that areas, which are potentially showing large motion or which are not present in some image frames, are not used for extracting PPG signals. Such areas are e.g. the edge areas of a person's face that is used as measurement area.

Still further, in an embodiment said signal extraction unit is configured to extract said PPG signals only from parts of the at least one measurement area showing no or the lowest amount of motion. Also this embodiment increases the quality of the PPG signals and of the obtained vital signs. Parts of the at least one measurement area typically showing a high amount of motion are e.g. the mouth area of a (talking) person or the eyes which are thus excluded from the evaluation and extraction of PPG signals according to this embodiment.

For motion estimation by the motion estimation unit one or more algorithms are preferably applied. In a first embodiment said motion estimation unit is configured to obtain a first time series representing a first average motion vector of the at least one measurement area in at least one direction within the image plane of said image frames, preferably in two orthogonal directions within the image plane of said image frames. In another embodiment said motion estimation unit is configured to obtain second time series representing local motion vector values of a plurality of pixels or pixel groups of the at least one measurement area. Preferably, block matching, 3DRS, optical flow and/or feature tracking is applied for estimating motion of the subject.

Similarly, for the spatial characteristic extraction one or more algorithms are preferably applied. Preferably, said spatial characteristic extraction unit is configured to obtain a third time series representing a second average motion vector of the at least one measurement area in at least one direction within the image plane of said image frames, preferably in two orthogonal directions within the image plane of said image frames, said second average motion vector indicating the spatial displacement of the spatial characteristic of a group of pixels (forming a pixel group) of said at least one measurement area. Said spatial characteristic extraction unit is advantageously configured to globally extract motion of the subject based on a displacement of the center of mass, center of an object (e.g. face) detection or barycenter of landmarks of a group of pixels, in particular exhibiting the same or similar color, pixel value and/or gradient. In other words, there are various options for determining a spatial characteristic of a pixel group, including the center of mass, the center of an object detection, a barycenter of landmarks detected on the pixel group, etc.

Further, in an embodiment said spatial characteristic extraction unit is configured to determine a displacement of the spatial characteristic of a group of pixels based on a displacement of one or more landmarks within said image frames, e.g. based on harris corner detection points, center of a face detector, etc.

For reliably characterizing motion appearing in the image frames said motion characterization unit is preferably configured to obtain a similarity measure between the output of said motion estimation unit and said spatial characteristic extraction unit by computing the differences between the outputs.

In a more detailed embodiment said motion characterization unit is configured to compute a first difference value from a first linear or non-linear combination of the first time series and the third time series and a second difference value from a first linear or non-linear combination of the second time series and the third time series and to combine the first and second difference values linearly or non-linearly to obtain a similarity measure indicating the similarity of the outputs of said motion estimation unit and said spatial characteristic extraction unit.

For determining the similarity measure said motion characterization unit is preferably configured to compute the product of the absolute values of the first difference and second difference values, the inverse of said product representing the similarity value.

To reliably distinguish between in-plane and out-of-plane motion of the subject said motion characterization unit is configured in an embodiment to compare the similarity measure against a predetermined similarity threshold.

To distinguish different motions of said different pixel groups said motion characterization unit is configured in an embodiment to determine local similarities for pixel groups.

In a preferred embodiment the proposed device further comprises an imaging unit, in particular a camera, for remotely detecting electromagnetic radiation emitted or reflected from the subject. The imaging unit is particularly suited for remote monitoring applications. The imaging unit can comprise one or more imaging elements. For instance, the imaging unit can comprise an array of photodiodes or charge-coupled devices. According to one embodiment, the imaging unit comprises at least two groups of imaging elements each of which is configured for detecting a single one of the data signal components. According to another embodiment, the imaging unit can make use of a single group of imaging elements having a response characteristic allowing for a detection of data signal components. The imaging unit can be further configured for capturing a sequence of image frames alternatingly representing the data signal components.

In another preferred embodiment the proposed device further comprises a radiation source, in particular a light source, for directing electromagnetic radiation to the subject. The radiation source can be embodied by a broadband illumination source and/or can make use of a single group or two or even more groups of radiation elements. However, the proposed device does not necessarily have to comprise radiation source, but can also make use of ambient light sources which are not connected to the device.

BRIEF DESCRIPTION OF THE DRAWINGS

These and other aspects of the invention will be apparent from and elucidated with reference to the embodiment(s) described hereinafter. In the following drawings FIG. 2 shows images displaying a translational motion and motion information derive there from, FIG. 3 shows images displaying a rotational motion and motion information derive there from, and FIG. 4 illustrates signal diagrams illustrating the extraction of vital sign information from complete and incomplete PPG signals.

DETAILED DESCRIPTION OF THE INVENTION

Figure 1:
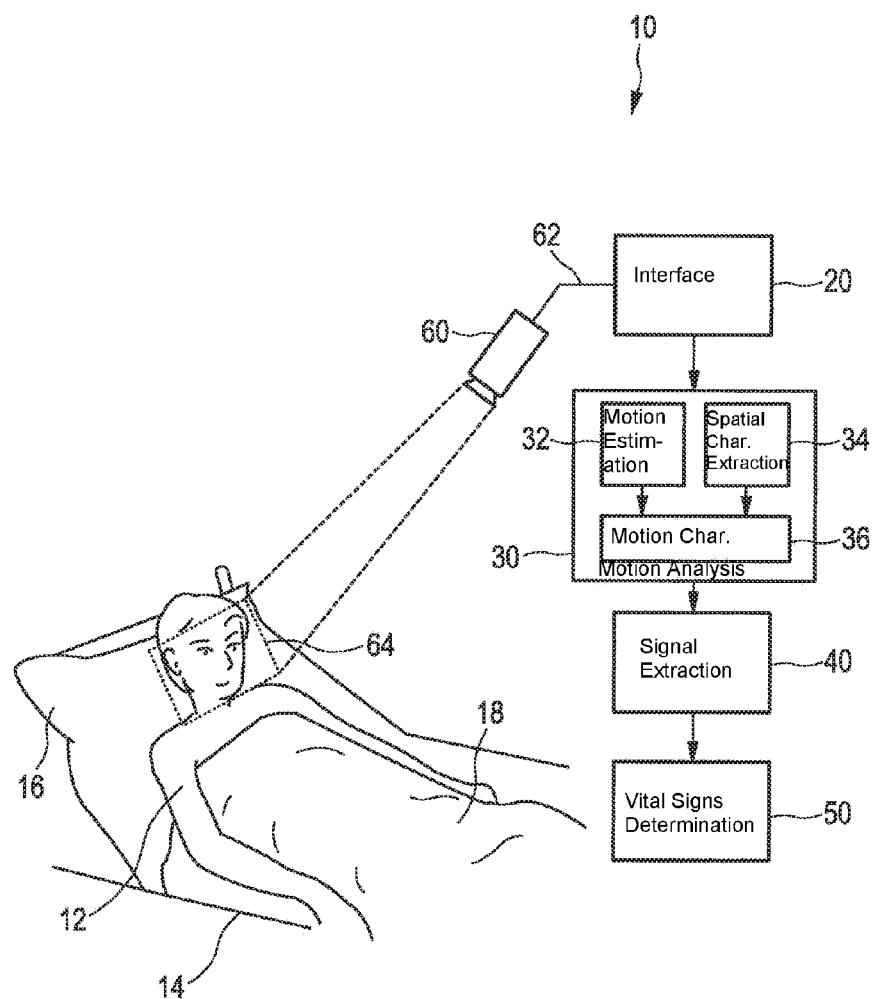
FIG. 1 shows an exemplary embodiment of a device for obtaining vital sign information of a subject according to the present invention.
Figure 4A:
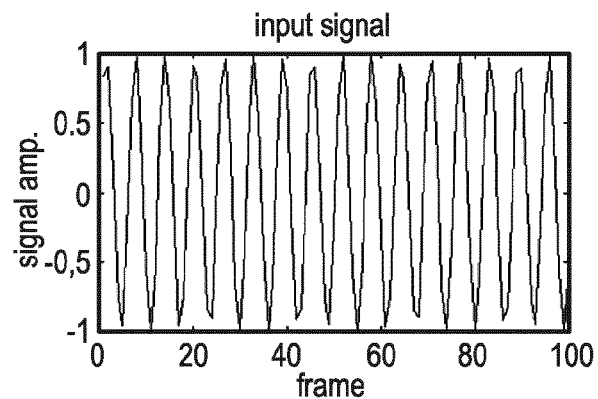
Figure 4B:
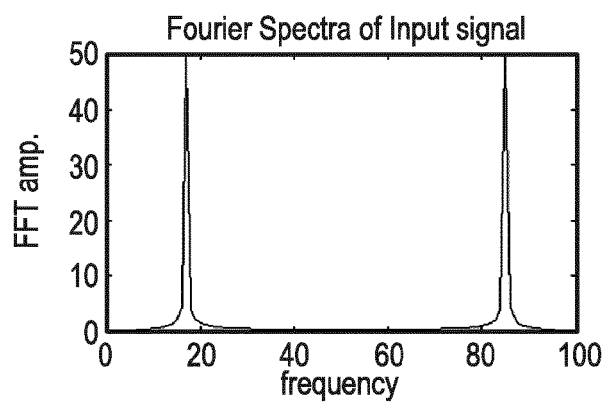
Figure 4C:
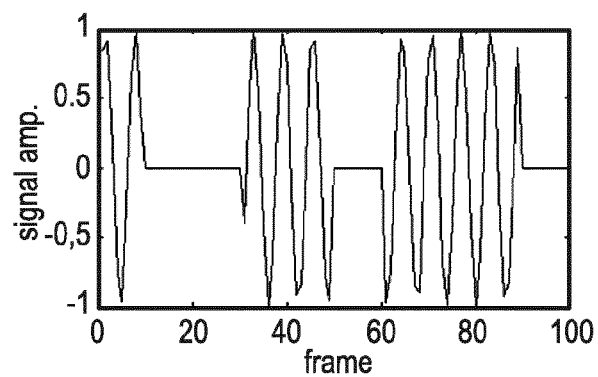
Figure 4D:
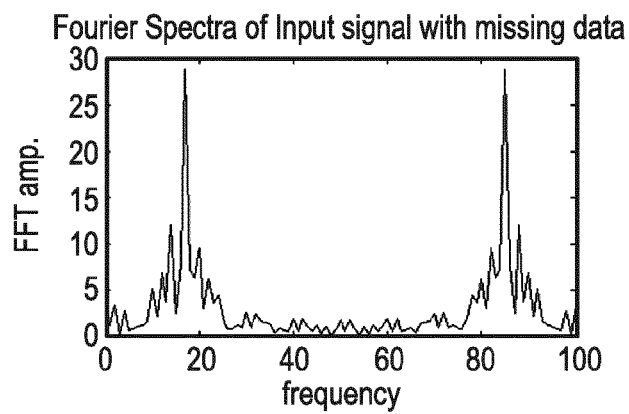

FIG. 1 shows a first exemplary embodiment of a device 10 for obtaining vital sign information of a subject 12 according to the present invention, in this exampled in a healthcare setting. The subject 12 lies in a bed 14, wherein the head of the subject 12 is located on a pillow 16 and the subject is covered with a blanket 18. The device 10 comprises an interface 20 for receiving a set of image frames 62 of the subject 12, a motion analysis unit 30 for analysing at least one measurement area 64 (also called region of interest) within the image frames of said set of image frames and for characterizing motion of the subject within said set of image frames, a signal extraction unit 40 for extracting photoplethysmographic (PPG) signals from said set of image frames using said characterization of motion of the subject within said set of image frames and a vital signs determination unit 50 for determining vital sign information from said extracted PPG signals.

Said motion analysis unit 30 comprises a motion estimation unit 32 for locally and/or globally estimating motion of the subject based on spatial similarities of pixels or pixel groups over consecutive image frames, a spatial characteristic extraction unit 34 for globally extracting motion of the subject based on a displacement of a spatial characteristic (e.g. the center of mass, a barycenter of landmarks, a center of a face detection) of a group of pixels exhibiting the same or similar properties, and a motion characterization unit 36 for determining the type of motion of the subject within said set of image frames based on the outputs of said motion estimation unit 32 and said spatial characteristic extraction unit 34.

In this embodiment the interface 20 is coupled to an imaging unit 60, in particular a camera, for acquiring a set of image frames from the subject, e.g. at a frame rate of at least 7 Hz in a desired spectral range (e.g. at a visible and/or infrared, or at multiple wavelengths or a single wavelength). In another embodiment the interface 20 may receive the set of image frames from a memory or a buffer storing at least two image frames or a complete set of image frames, which have been previously acquired.

To properly characterize the motion performed by the subject being monitored several modules are provided as shown in FIG. 1. These modules shall be explained in more detail in the following.

The motion estimation unit 32 aims at extracting detailed motion information (at global and/or local level), preferably based on spatial pixel similarity over consecutive image frames. Any of the techniques including block matching, 3DRS (3D recursive search), optical flow, feature tracking, template matching may be used for this purpose. The output of the motion estimation unit 32 is composed, in one embodiment, of a time series representing the average motion vector in two directions, preferably in both vertical and horizontal direction, of the measurement area of the monitored subject (e.g. of the face of the subject) and/or the local motion vector values of a set of pixels comprised in the measurement area of the monitored subject.

The spatial characteristic extraction unit 34 aims at extracting motion at global level, particularly based on the displacement of the spatial characteristic of a group of pixels exhibiting similar properties. In preferred embodiments said similar properties are determined based on perceived color (e.g. all skin pixels are regarded as having similar color), based on pixel value and/or gradient information (e.g. projected histogram), and/or based on the displacement of specific landmarks. The output of the spatial characteristic extraction unit 34 is composed, in one embodiment, of a time series representing the average motion vector, expressed with the spatial displacement of the spatial characteristic of a set of pre-defined pixels in two directions, preferably in both vertical and horizontal direction, of the measurement area of the monitored subject (e.g. of the face of the subject).

The motion characterization unit 36 uses the outputs generated by the motion estimation unit 32 and the spatial characteristic extraction unit 34 to determine the type of motion performed by the subject being monitored. This characterization may be operated by analyzing how similar the outputs generated by the two units are.

In one embodiment this similarity measure is obtained by calculating the difference between the motion information gathered by both components as follow:

$$S=f(g(GME,COM),g(LME,COM)) \quad (1)$$

with S being the similarity measure, GME and LME being respectively the time series (time vectors) containing the global (GME) and local motion information (LME) obtained by the motion estimation unit 32, COM being the center of mass motion obtained by the spatial characteristic extraction unit 34, g(x) being any linear/non-linear operation allowing the extraction of distance, and f(x) being any linear/non-linear operation combining two distances into one number.

One possible embodiment for calculating the similarity measure using a non-linear combination is e.g.

$$S=1/(\|GME-COM\| \times SUM(\|LME-COM\|)) \quad (2),$$

whereby in the term ∥LME−COM∥ the difference is performed by taking the difference between each local motion estimation output (LME) and the value of the center of mass motion (COM).

Another possible embodiment for calculating the similarity measure using a linear combination is e.g.

$$S=\|GME-COM\|+SUM(\|LME-COM\|)) \quad (3),$$

In one embodiment, this similarity measure is compared against a threshold value allowing the distinction between in-plane motion (i.e. motion within the image plane of the images frames of the set) and out-of-plane motion (i.e. motion out of the image plane of the images frames of the set). Hereby, the threshold value may be obtained experimentally on a large dataset of sets of image frames, or may be set by a user, e.g. based on past experience. In another embodiment, this similarity measure is sent to a classifier performing the motion characterization using GME, LME and COM as described above. In still another embodiment, a local similarity measure is calculated to distinguish groups of pixels exhibiting different motion (e.g. a talking scenario).

To illustrate how this similarity measure behaves depending on the subject motion two different motions shall be considered in the example illustrated in FIGS. 2 and 3, namely subject face translation in the camera plane (i.e. the image plane) and subject face rotation out of the camera plane. FIG. 2 illustrates a translation scenario in which the face of the subject performs a translational movement within the image plane. FIG. 3 illustrates a rotation scenario in which the face of the subject performs a rotational movement out of the image plane.

FIGS. 2A and 2B show two consecutive image frames with the face at different translational positions. FIG. 2C shows the corresponding (local) motion field obtained by the motion estimation unit 32. FIGS. 2D and 2E show corresponding skin masks of the same two consecutive image frames shown in FIGS. 2A and 2B, wherein the center of mass M is indicated in FIGS. 2D and 2E. FIG. 2F shows the corresponding center of mass displacement obtained by the spatial characteristic extraction unit 34.

FIGS. 3A and 3B show two consecutive image frames with the face at different rotational positions. FIG. 3C shows the corresponding (local) motion field obtained by the motion estimation unit 32. FIGS. 3D and 3E show corresponding skin masks of the same two consecutive image frames shown in FIGS. 3A and 3B, wherein the center of mass M is indicated in FIGS. 3D and 3E. FIG. 3F shows the corresponding center of mass displacement obtained by the spatial characteristic extraction unit 34.

In the two examples illustrated in FIGS. 2 and 3 it can be seen how the similarity measure behaves. Using the formula (2), it is clear that for the translation scenario (FIG. 2) the similarity measure will converge towards infinity, while in the rotation scenario (FIG. 3) the similarity measure will take a significantly low value (ranging e.g. from 1 to 10).

Once the similarity measure is extracted the image stream is processed by the signal extraction unit 40 for extracting PPG signals using the previously determined characterization of motion of the subject, in particular depending on the value of the similarity measure. Preferably, in one embodiment, any conventional technique as disclosed in the above cited document or as generally known in the art for PPG signal extraction may be used in case in-plane-motion has been detected, while no processing (i.e. no PPG signal extraction) is applied when out-of-plane motion has been detected.

When no PPG signal is extracted in case of out-of-plane motion, this may lead to a "null" signal, i.e. part of the extracted signal may be set to null for the image frames which are characterized to contain out-of-plane motion. When such "null" signal is extracted from the image stream several options can be used to extract meaningful vital signs information (e.g. heart rate information, respiratory information, SpO2 information, etc.). Among several options, direct Fourier analysis on the time signal containing this "null" data point can be used, as well as interpolation techniques to re-create these missing data points or techniques allowing for Fourier analysis on unevenly sampled data as e.g. described in the Wikipedia article regarding non-uniform discrete Fourier transform, currently found at http://en.wikipedia.org/wiki/Non-uniform_discrete_Fourier_transform.

FIG. 4 illustrates an example showing that, while having this "null" data point in the time signal, it is still possible to extract a dominant frequency, being the heart rate frequency as example here. FIG. 4A shows a complete periodic PPG signal. FIG. 4B shows the corresponding Fourier spectrum of the PPG signal of FIG. 4A, from which the desired vital sign signal (here the heart rate frequency indicated by the dominant frequency in the expected frequency range) can be derived. FIG. 4C shows an incomplete periodic PPG signal which includes "null" data points at which no PPG signal was extracted from the corresponding image frames. FIG. 4D shows the corresponding Fourier spectrum of the PPG signal of FIG. 4C, from which the desired vital sign signal (here the heart rate frequency indicated by the dominant frequency in the expected frequency range) can be derived as well. From FIG. 4D it can be clearly seen that despite the missing data points the dominant frequency can still be easily extracted from a signal containing more than 40% of missing data points.

In another embodiment of the proposed device a talking action (or, more generally, any facial deformation) is detected. In this case the processing is focused only on the facial areas exhibiting the dominant motion pattern. This is achieved by computing a 2D histogram of the motion (preferably in X and Y direction) and selecting the dominant motion pattern (using e.g. a clustering algorithm of principle component analysis (PCA)). As a result this embodiment will then select all pixels that do not exhibit motion for PPG signal extraction, while rejecting all pixels for PPG signal extraction next to the mouth area where motion is detected.

In still another embodiment, where face rotation is detected, only the skin pixels present in the central region of the skin mask are used for PPG signal extraction. Such selection ensures that no pixel next the boundary of the skin mask are used for the extraction of vital signs. Pixels next to skin mask boundaries are prone to motion estimation inaccuracy and have more chances to actually disappear and reappear during the motion, which would thus introduce extra noise in the vital sign extraction.

To select this central part of the skin mask, image erosion (on the binary mask) can be applied, using a kernel which size depends on the rotation speed (e.g. linear relationship). Doing so, only a small portion of pixels is discarded for subtle rotation, while a significant piece is rejected when strong rotation occurs.

Once the right processing has been applied to generate a time signal (PPG signal) representing a vital signs parameter, the vital signs determination unit 50 determines vital sign information from said extracted PPG signals using e.g. a conventional known method as e.g. described in any of the above cited documents.

One other interesting aspect of the proposed motion-specific processing is that a reliability indication measure can be extracted depending on the type of motion being observed. A corresponding reliability estimation module may be used for providing such reliability information based on the ability of the proposed device to accurately derive vital signs information considering the characterized motion.

In still another embodiment, the reliability measure as expressed in formulas (1) or (2) can be used to extract this reliability indication measure. In another embodiment the type of motion is linked to an arbitrary value. For instance, in case of translation a reliability indicator can be set to 1, and in case of rotation the reliability indicator can be set to a lower value, e.g. to 0.1. Said reliability indicator can be used to indicate the reliability of a PPG signal and/or an extracted vital sign information extracted from said PPG signal.

By way of example, the present invention can be applied in the field of health care, e.g. unobtrusive remote patient monitoring, neonate monitoring, general surveillances, security monitoring and so-called lifestyle environments, such as fitness equipment, or the like.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for obtaining a vital sign of a subject, the device comprising:
   an interface for receiving a set of image frames of a subject;
   a motion analysis unit for analysing at least one measurement area within the image frames of said set of image frames and for characterizing motion of the subject within said set of image frames, said motion analysis unit comprising
      a motion estimation unit for locally and/or globally estimating motion of the subject based on spatial similarities of pixels or pixel groups over consecutive image frames,
      a spatial characteristic extraction unit for globally extracting motion of the subject based on a displacement of a spatial characteristic of a group of pixels exhibiting the same or similar properties, and
      a motion characterization unit for determining a type of motion of the subject within said set of image frames by calculating a similarity measure of a similarity of the outputs of said motion estimation unit and said spatial characteristic extraction unit;
   a signal extraction unit for extracting photoplethysmographic (PPG), signals from said set of image frames including using said determination of motion of the subject within said set of image frames to one of:
      extract said PPG signals only from image frames showing no or substantially no out-of-plane motion;
      replace parts of said PPG signals extracted from image frames showing out-of-plane motion by interpolated signal parts of the PPG signals when out-of-plane motion is detected; or
      reduce the size of the at least one measurement area from which PPG signals are extracted in case of out-of-plane motion of the subject to extract PPG signals only from a central area of the at least one measurement when out-of-plane motion is detected;
   and
   a vital signs determination unit for determining vital sign information from said extracted PPG signals.

2. The device as claimed in claim 1,
   wherein said signal extraction unit is configured to extract said PPG signals only from parts of the at least one measurement area showing no or the lowest amount of motion.

3. The device as claimed in claim 1,
   wherein said motion estimation unit is configured to obtain a first time series representing a first average motion vector of the at least one measurement area in at least one direction within the image plane of said image frames, preferably in two orthogonal directions within the image plane of said image frames.

4. The device as claimed in claim 3,
   wherein said motion characterization unit is configured to compute a first difference value from a first linear or non-linear combination of the first time series and a third time series and a second difference value from a first linear or non-linear combination of a second time series and the third time series and to combine the first and second difference values linearly or non-linearly to obtain a similarity measure indicating the similarity of the outputs of said motion estimation unit and said spatial characteristic extraction unit.

5. The device as claimed in claim 4, wherein said motion characterization unit is configured to compare the similarity measure against a predetermined similarity threshold to distinguish between in-plane and out-of-plane motion of the subject and/or to determine local similarities for pixel groups to distinguish different motions of said different pixel groups.

6. The device as claimed in claim 1, wherein said motion estimation unit is configured to obtain second time series representing local motion vector values of a plurality of pixels or pixel groups of the at least one measurement area.

7. The device as claimed in claim 1, wherein said motion estimation unit is configured to apply block matching, 3DRS, optical flow, template matching and/or feature tracking for estimating motion of the subject.

8. The device as claimed in claim 1, wherein said spatial characteristic extraction unit is configured to obtain a third time series representing a second average motion vector of the at least one measurement area in at least one direction within the image plane of said image frames, preferably in two orthogonal directions within the image plane of said image frames, said second average motion vector indicating the spatial displacement of the spatial characteristic of a group of pixels of said at least one measurement area.

9. The device as claimed in claim 1, wherein said spatial characteristic extraction unit is configured to globally extract motion of the subject based on a displacement of the center of mass, center of an objection detection or barycenter of landmarks of a group of pixels, in particular exhibiting the same or similar color, pixel value and/or gradient.

10. The device as claimed in claim 1, wherein said spatial characteristic extraction unit is configured to determine a displacement of the spatial characteristic of a group of pixels based on a displacement of one or more landmarks within said image frames.

11. The device as claimed in claim 1, wherein said motion characterization unit is configured to obtain a similarity measure between the output of said motion estimation unit and said spatial characteristic extraction unit by computing the differences between the outputs.

12. A method for obtaining a vital sign of a subject, the method comprising:
receiving a set of image frames of a subject;
analysing at least one measurement area within the image frames of said set of image frames and for characterizing motion of the subject within said set of image frames by
locally and/or globally estimating motion of the subject based on spatial similarities of pixels or pixel groups over consecutive image frames,
globally extracting motion of the subject based on a displacement of a spatial characteristic of a group of pixels exhibiting the same or similar properties, and
determining a type of motion of the subject within said set of image frames by calculating a similarity measure of a similarity of the outputs of said motion estimation and said spatial characteristic extraction;
extracting photoplethysmographic (PPG) signals from said set of image frames using said determination of motion of the subject within said set of image frames;
wherein the extracting of photoplethysmographic, PPG, signals includes one of:
extracting said PPG signals only from image frames showing no or substantially no out-of-plane motion or
replacing parts of said PPG signals extracted from image frames showing out-of-plane motion by interpolated signal parts of the PPG signals, or
reducing the size of the at least one measurement area, from which PPG signals are extracted by extracting PPG signals only from a central area of the at least one measurement area, and
determining vital sign information from said extracted PPG signals.

13. A non-transitory computer-readable medium storing instructions for causing a computer to carry out the steps of the method as claimed in claim 12 when said computer program is carried out on the computer.

14. A device configured to obtain a vital sign of a subject, the device comprising:
an interface configured to receive a set of image frames of a subject; and
at least one electronic processor programmed to analyze at least one measurement area within the image frames of said set of image frames and characterize motion of the subject within said set of image frames by operations including:
locally and/or globally estimating motion of the subject based on spatial similarities of pixels or pixel groups over consecutive image frames,
globally extracting motion of the subject based on a displacement of a spatial characteristic of a group of pixels exhibiting the same or similar properties
determining a type of motion of the subject within said set of image frames by calculating a similarity measure of a similarity of the outputs of said motion estimation and said spatial characteristic extraction;
extracting photoplethysmographic (PPG) signals from said set of image frames by operations including using said determination of motion of the subject within said set of image frames to one of:
extract said PPG signals only from image frames showing no or substantially no out-of-plane motion;
replace parts of said PPG signals extracted from image frames showing out-of-plane motion by interpolated signal parts of the PPG signals when out-of-plane motion is detected; or
reduce the size of the at least one measurement area from which PPG signals are extracted in case of out-of-plane motion of the subject to extract PPG signals only from a central area of the at least one measurement when out-of-plane motion is detected; and
determining vital sign information from said extracted PPG signals.

15. The device as claimed in claim 14, wherein the at least one electronic processor is programmed to:
extract said PPG signals only from parts of the at least one measurement area showing no or the lowest amount of motion.

16. The device as claimed in claim 14, wherein the at least one electronic processor is programmed to:

obtain a first time series representing a first average motion vector of the at least one measurement area in at least one direction within the image plane of said image frames.

17. The device as claimed in claim 14, wherein the at least one electronic processor is programmed to:
    obtain second time series representing local motion vector values of a plurality of pixels or pixel groups of the at least one measurement area.

18. The device as claimed in claim 17, wherein the at least one electronic processor is programmed to:
    compute a first difference value from a first linear or non-linear combination of a first time series and a third time series and a second difference value from a first linear or non-linear combination of the second time series and the third time series; and
    combine the first and second difference values linearly or non-linearly to obtain a similarity measure indicating the similarity of the outputs of said motion estimation and said spatial characteristic extraction.

19. The device as claimed in claim 18, wherein the at least one electronic processor is programmed to:
    compare the similarity measure against a predetermined similarity threshold to distinguish between in-plane and out-of-plane motion of the subject and/or to determine local similarities for pixel groups to distinguish different motions of said different pixel groups.

20. The device as claimed in claim 14, wherein the at least one electronic processor is programmed to:
    obtain a third time series representing a second average motion vector of the at least one measurement area in at least one direction within the image plane of said image frames, said second average motion vector indicating the spatial displacement of the spatial characteristic of a group of pixels of said at least one measurement area.

* * * * *